United States Patent [19]

Corbin et al.

[11] Patent Number: 5,600,040
[45] Date of Patent: Feb. 4, 1997

[54] SEPARATION OF TETRAFLUOROETHANE ISOMERS

[75] Inventors: David R. Corbin, West Chester; Barry A. Mahler, Glen Mills, both of Pa.

[73] Assignee: E. I. Du Pont de Nemours and Company, Wilmington, Del.

[21] Appl. No.: 374,617

[22] PCT Filed: Jul. 17, 1992

[86] PCT No.: PCT/US92/05851

§ 371 Date: Feb. 17, 1995

§ 102(e) Date: Feb. 17, 1995

[87] PCT Pub. No.: WO94/02440

PCT Pub. Date: Feb. 3, 1994

[51] Int. Cl.$^6$ .......................... C07C 17/389; C07C 19/08
[52] U.S. Cl. ........................................................ 570/179
[58] Field of Search ............................................. 570/179

[56] References Cited

U.S. PATENT DOCUMENTS

| | | | |
|---|---|---|---|
| 3,026,359 | 3/1962 | Mastrangelo et al. | 570/179 |
| 3,215,747 | 11/1965 | Fainberg et al. | 570/179 |
| 4,605,798 | 8/1986 | Abel et al. | 570/164 |
| 4,902,312 | 2/1990 | Chang | 55/71 |
| 4,906,796 | 3/1990 | Yates | 570/179 |
| 4,940,824 | 7/1990 | Yates | 570/179 |
| 4,940,825 | 7/1990 | Yates | 570/179 |
| 4,950,816 | 8/1990 | Tung et al. | 570/179 |
| 5,187,131 | 2/1993 | Tiggelbeck et al. | 570/179 |
| 5,233,107 | 8/1993 | Jansen | 570/179 |

FOREIGN PATENT DOCUMENTS

| | | | |
|---|---|---|---|
| 0389334 | 9/1990 | European Pat. Off. | C07C 19/08 |
| 389334 | 9/1990 | European Pat. Off. | 570/179 |
| 3311751 | 10/1984 | Germany | C07C 17/38 |
| 3-72437 | 3/1991 | Japan | C07C 19/08 |
| 4-308537 | 10/1992 | Japan | C07C 17/38 |
| 1578933 | 11/1980 | United Kingdom | C07C 19/08 |
| WO91/15445 | 10/1991 | WIPO | C07C 17/38 |

OTHER PUBLICATIONS

Hiromoto, Ono et al, "Purification of 1,1,1,2-tetrafluoroethane", *Chemical Abstracts*, 115(17), Oct. 18, 1991, Abstract No. 182607b.

*Primary Examiner*—Joseph E. Evans

[57] ABSTRACT

Separation of $CF_3CH_2F$ and $CHF_2CHF_2$ from a mixture thereof is effectively achieved using either inorganic molecular sieves having suitable intermediate electronegaativities (compared to Zeolite Na-X) or activated carbon.

10 Claims, No Drawings

SEPARATION OF TETRAFLUOROETHANE ISOMERS

This application represents the U.S. national filing (371) of International Application No. PCT/US92/05851 filed Jul. 17, 1992 and published as WO94/02440 Feb. 3, 1994.

FIELD OF THE INVENTION

This invention relates to the separation of fluorocarbon products, more particularly to the separation of the isomers of tetrafluoroethane, $CHF_2CHF_2$ (HFC-134) and $CF_3CH_2F$ (HFC-134a).

BACKGROUND

Isomers of $C_2H_2F_4$ (HFC-134s) are used as refrigeration fluids for a number of applications. HFC-134s can also be used as starting materials for producing various other halogenated hydrocarbons. Products containing isomers of $C_2H_2F_4$ are produced in various degrees of isomer purity. One method of producing HFC-134s is by the hydrogenolysis of $C_2C_{12}F_4$ isomers (CFC-114s). In the manufacture of $C_2Cl_2F_4$ by the chlorofluorination of perchloroethylene the product typically consists of a mixture of the isomers, $CClF_2CClF_2$ (CFC-114) and $CF_3CCl_2F$ (CFC-114a) (see e.g., U.S. Pat. No. 4,605,798). If the CFC-114s are then used to produce $CHF_2CClF_2$ (HCFC-124a), $CF_3CHClF$ (HCFC-124), HFC-134 or HFC-134a by hydrodehalogenation, the products often consist of a mixture of $C_2HClF_4$ and $C_2H_2F_4$ isomers (see e.g., GB 1,578,933).

It has been found that for many applications, the presence of the second isomer of the isomer pair can significantly alter the physical and chemical properties of the desired isomer. For example, variation in the HFC-134/HFC-134a ratio in the product can result in dramatic variability in the thermodynamic properties critical for use in refrigeration applications. For use as a raw material feed, the presence of the unwanted isomer can result in yield loss due to increased side reactions. As a result, there has been a continually increasing demand for high isomer purity materials. Consequently, the separation of HFC-134 isomers represents a significant aspect of preparing these compounds for various applications.

Purification of halogenated hydrocarbon products has been the subject of considerable research. Of particular interest are the challenges presented in separating desired halogenated hydrocarbon products from materials such as impurities in the starting materials used to produce the halogenated hydrocarbon, excess reactants, and reaction by-products and/or reaction co-products which are difficult to remove by standard separation methods such as distillation. Selective sorbents such as carbons and zeolites have been proposed for various separations. The effectiveness of separation using such sorbents varies with the chemical components and the sorbents involved. The successful design of sorbent based systems is considered highly dependent upon experimental determination of whether the relative sorbencies of the particular compounds are suitable for such systems.

HFC-134 has a boiling point of −23° C. and HFC-134a has a boiling point of −26.5° C. Distillation is consequently relatively inefficient as a means for separating these two compounds.

SUMMARY OF THE INVENTION

We have found that mixtures of the isomers of $C_2H_2F_4$ (i.e., $CHF_2CHF_2$ and $CF_3CH_2F$) can be substantially separated by using a sorbent for $CHF_2CHF_2$ selected from the group consisting of (i) inorganic molecular sieves (e.g., zeolites) having greater intermediate electronegativities than Zeolite Na-X, and (ii) activated carbons. The present invention provides a process for separating a mixture of $CHF_2CHF_2$ and $CF_3CH_2F$ to provide a product wherein the mole ratio of $CF_3CH_2F$ relative to $CHF_2CHF_2$ is increased which comprises contacting said mixture with said sorbent at a temperature within the range of −20° C. to 300° C. and a pressure within the range of 10 kPa to 3000 kPa and for a period of time sufficient to remove a substantial amount of the $CHF_2CHF_2$. As a result, the mole ratio of $CF_3CH_2F$ to $CHF_2CHF_2$ increases (preferably by 25% or more); and a product wherein the mole ratio of $CF_3CH_2F$ relative to $CHF_2CHF_2$ is increased, may thus be recovered.

This invention also provides a process for separating a mixture of $CHF_2CHF_2$ and $CF_3CH_2F$ to provide a product wherein the mole ratio of $CHF_2CHF_2$ relative to $CF_3CH_2F$ is increased which comprises contacting said mixture with said sorbent as described above to remove a substantial amount of the $CHF_2CHF_2$, and desorbing sorbed $CHF_2CHF_2$ to provide a product which is enriched therewith. Another process of this invention for separating a mixture of $CHF_2CHF_2$ and $CF_3CH_2F$ to provide a product wherein the mole ratio of $CHF_2CHF_2$ relative to $CF_3CH_2F$ is increased, comprises contacting said mixture with a sorbent for $CF_3CH_2F$ selected from the group consisting of inorganic molecular sieves having intermediate electronegativities equal to or less than the intermediate electronegativity of Zeolite Na-X, at a temperature within the range of −20° C. to 300° C. and a pressure within the range of 10 kPa to 3000 kPa and for a period of time sufficient to remove a substantial amount of the $CF_3CH_2F$.

Said process for producing a $CF_3CH_2F$ enriched product and said processes for producing a $CHF_2CHF_2$ enriched product may be integrated into an overall process (e.g., a thermal swing cycle process) whereby both of said products are provided. Said process for producing a $CF_3CH_2F$ enriched product and/or said processes for producing a $CHF_2CHF_2$ enriched product may also be used in conjunction with a process for producing HFC-134 and HFC-134a by the hydrogenolysis of CFC-114 and/or CFC-114a.

DETAILS OF THE INVENTION

The present invention provides for the separation of HFC-134 from HFC-134a. Isomer enriched products are provided in accordance with this invention by contacting a mixture of $C_2H_2F_4$ isomers with a sorbent for $CHF_2CHF_2$ selected from the group consisting of activated carbons and certain inorganic molecular sieves at a temperature and pressure suitable for sorption, for a period of time sufficient to remove a substantial amount of said $CHF_2CHF_2$. $CF_3CH_2F$ enriched product is thereby provided using $CHF_2CHF_2$ sorption. Where $CHF_2CHF_2$ enriched product is desired, the invention also includes a process involving desorbing sorbed $CHF_2CHF_2$ to provide a product which is enriched therewith. The process based upon preferential $CHF_2CHF_2$ sorption is particularly useful for purifying $CF_3CH_2F$ which contains minor amounts of $CHF_2CHF_2$. Where the process is used for such purification of $CF_3CH_2F$, the isomer mix to be purified by this process generally has a mole ratio of $CF_3CH_2F$ to $CHF_2CHF_2$ of at least about 9:1, preferably at least about 19:1, and most preferably at least about 99:1.

A mix of the $C_2H_2F_4$ isomers may result, for example, from a process involving the reaction of the CFC-114 and/or CFC-114a isomers with hydrogen. Unreacted starting materials and $C_2HClF_4$ isomers may be recycled and reacted further with hydrogen to produce additional $C_2H_2F_4$. Additional impurities may be present in these products. Distillation is typically used in order to remove impurities such as HCl, HF, under- and over-chlorinates and fluorinates to produce products that are at least 90% $C_2H_2F_4$. Separation of $C_2H_2F_4$ isomers in accordance with this invention to provide products which are enriched in HFC-134 and/or products which are enriched in HFC-134a then may be advantageously employed. This invention can thus be adapted for use in connection with production of $C_2H_2F_4$ by hydrogenolysis of materials such as $C_2Cl_2F_4$ such that after removal of a substantial amount of $CHF_2CHF_2$ using the sorbent, either (i) a product is recovered wherein the mole ratio of $CF_3CH_2F$ relative to $CHF_2CHF_2$ is increased, (ii) sorbed $CHF_2CHF_2$ is desorbed to produce a product wherein the mole ratio of $CHF_2CHF_2$ relative to $CF_3CH_2F$ is increased, or both (i) and (ii).

Some embodiments of this invention use activated carbon as the sorbent. Commercially available activated carbon may be used. The effectiveness of the process can be influenced by the particular activated carbon employed. Moreover, the sorption efficiency and sorption capacity of an activated carbon bed depends upon the particle size of an activated carbon in a dynamic flow system. Preferably, the activated carbon has a particle size range of from about 4 to 325 mesh (from about 0.044 to 4.76 millimeters). More preferably, the activated carbon has a particle size range of from about 6 to 100 mesh (from about 0.149 to 3.36 millimeters). Most preferably, the activated carbon has a particle size range of from about 10 to 30 mesh (from about 0.595 to 2.00 millimeters).

An activated carbon obtained having a particle size range of about 0.074×0.297 millimeters (50×200 mesh) is available from the Barneby & Sutcliffe Corp. as Activated Carbon Type UU (natural grain, coconut shell based). An activated carbon having a particle size of 0.595 millimeters× 1.68 millimeters (12×30 mesh) is available from the Calgon Corporation as Calgon BPL (bituminous coal based) activated granular carbon. An activated carbon having a particle size range of about 0.450×1.68 millimeters (12×38 mesh) is available from Barnebey & Sutcliffe Corp. as Barneby & Sutcliffe Corp. Activated Carbon Type PE (natural grain, coconut shell carbon). An activated carbon having a particle size range of about 0.297×0.841 millimeters (20×50 mesh) is available from Westvaco as Microporous Wood-Base Granular Carbon.

Typically the activated carbon used will have a total content of from about 0.1 to 10 weight percent of alkali and alkaline earth metals selected from lithium, sodium, potassium, rubidium, cesium, magnesium, calcium, strontium and/or barium. The alkali and alkaline earth metal content of carbon can be regulated by techniques known in the art. For example, the metal content of carbon can be reduced by acid washing; and the metal content can be increased by standard impregnation techniques. In a preferred embodiment using preferential HFC-134 sorption, the activated carbon contains inherent alkali and/or alkaline earth metal(s) selected from the group consisting of lithium, sodium, potassium, rubidium, cesium, magnesium, calcium, strontium, barium, and combinations thereof. Inherent alkali metals (typically Na and/or K) are preferred. The presence of these metals, particularly as inherent metals in the range of from about 0.5 to 3 percent by weight, is considered to improve the HFC-134 sorption efficiency.

Some embodiments of this invention use inorganic molecular sieves. Molecular sieves are well known in the art and are defined in R. Szosak, Molecular Sieves-Principles of Synthesis and Identification, Van Nostrand Reinhold (1989) page 2. The inorganic molecular sieves used for preferentially sorbing HFC-134 in accordance with this invention include various silicates (e.g., titanosilicates and zeolites such as Zeolite Y, Zeolite A, Zeolite ZSM-5, and Zeolite ZSM-8), metalloaluminates and aluminophosphates, as well as other inorganic molecular sieve materials. The molecular sieves useful in the invention will typically have an average pore size of from about 0.3 to 1.5 nm.

The Sanderson electronegativity model (see, R. T. Sanderson, "Chemical Bonds and Bond Energy", 2nd ed., Academic Press, New York, 1976) furnishes a useful method for classifying inorganic molecular sieves based on their chemical composition. In accordance with this invention the preferential sorption of tetrafluoroethane isomers by molecular sieves can be correlated with their intermediate electronegativity (i.e., their "Sint") as determined by the Sanderson method based on chemical composition. The Sint for Zeolite Na-X is about 2.38.

Inorganic molecular sieves with Sints greater than the Sint for Zeolite Na-X (i.e., more electronegative or more acidic) may be used in accordance with this invention for increasing the mole ratio of $CF_3CH_2F$ relative to $CHF_2CHF_2$ by removing a substantial amount of $CHF_2CHF_2$; and/or for increasing the mole ratio of $CHF_2CFH_2$ relative to $CF_3CH_2F$ by desorbing sorbed $CHF_2CHF_2$ (i.e., $CHF_2CHF_2$ is believed to sorb more strongly than $CH_2FCF_3$).

Inorganic molecular sieves with Sints no greater than the Sint for Zeolite Na-X (i.e., less electronegative or more basic) may be used in accordance with this invention for increasing the mole ratio of $CHF_2CHF_2$ relative to $CF_3CH_2F$ by removing a substantial amount of $CF_3CH_2F$; and/or for increasing the mole ratio of $CF_3CH_2F$ relative to $CHF_2CHF_2$ by desorbing sorbed $CF_3CH_2F$ (i.e., $CF_3CH_2F$ is believed to sorb more strongly than $CHF_2CHF_2$). Accordingly, this invention provides a process for separating a mixture of $CHF_2CHF_2$ and $CF_3CH_2F$ to provide a product wherein the mole ratio of $CHF_2CHF_2$ relative to $CF_3CH_2F$ is increased, which comprises the step of contacting said mixture with a sorbent for $CF_3CH_2F$ selected from the group consisting of activated inorganic molecular sieves having intermediate electronegativities equal to or less than the intermediate electronegativity of Zeolite Na-X, at a temperature within the range of −20° C. to 300° C. and a pressure within the range of 10 kPa to 3000 kPa and for a period of time sufficient to remove a substantial amount of the $CF_3CH_2F$. Example Sint values are provided in Table I.

TABLE I

Intermediate Sanderson Electronegativities for Selected Molecular Sieves

| Molecular Sieve | Sint |
|---|---|
| Na-X | 2.38 |
| Ca-A | 2.56 |
| Na—Y | 2.58 |
| ETS | 2.60 |
| H—Y | 2.97 |
| Na-ZSM-8 | 3.00 |
| H-ZSM-5 | 3.04 |
| H-ZSM-8 | 3.04 |

Generally, for the inorganic molecular sieves, it is desirable to occupy acidic sites of the sieve material with alkali metal(s) and or alkaline earth metal(s) so long as the intermediate electronegativity remains suitable for the desired separation. In a preferred embodiment using preferential HFC-134 sorption the inorganic molecular sieve is a Zeolite Y which contains alkali or alkaline earth metal (s) selected from the group consisting of lithium, sodium, potassium, rubidium, cesium, magnesium, calcium, strontium and barium or combinations thereof. Alkali metals are preferred. It is preferred that alkali metals occupy from about 50% to 100% of the accessible exchange sites in the zeolite. Particularly preferred zeolite molecular sieves include those having alkali metal to aluminum ratios of about 1:1, or alkaline earth metal to aluminum ratios of about 1:2.

Suitable temperature ranges for sorption range from about −20° C. to about 300° C. Suitable pressures for sorption range from about 10 kPa to about 3000 kPa.

Contact with sorbent should be sufficient to achieve the desired degree of isomer enrichment. Preferably, the mole ratio of the enriched isomer to the second isomer is increased by at least about 25% relative to the mole ratio thereof in the initial mixture, most preferably by at least about 50%.

Where the process is used to purify $CF_3CH_2F$ from a mixture of $CF_3CH_2F$ and $CHF_2CHF_2$ using preferential HFC-134 sorption, preferably at least about 50 mole % of the $CHF_2CHF_2$ is removed. A particularly advantageous embodiment of this invention involves providing sufficient contact to produce $CF_3CH_2F$ of at least about 99.99 mole percent purity.

This invention can be practiced with the sorbent contained in a stationary packed bed through which the process stream whose components need separation is passed. Alternatively, it can be practiced with the sorbent applied as a countercurrent moving bed; or with a fluidized bed where the sorbent itself is moving. It can be applied with the sorbent contained as a stationary packed bed but the process configured as a simulated moving bed, where the point of introduction to the bed of the process stream requiring separation is changed, such as may be effected using appropriate switching valves.

The production of a product enriched with respect to one $C_2H_2F_4$ isomer may be accompanied by the production of other products which are enriched with regard to the concentration of one or more other components of the initial mixture. Indeed, a typical process might include both a product which is enriched in $CF_3CH_2F$ (e.g., essentially pure $CF_3CH_2F$) and another product which is enriched in $CHF_2CHF_2$. The production of product enriched in $CHF_2CHF_2$ generally involves desorption of $CHF_2CHF_2$. In any case, whether or not a $CHF_2CHF_2$ enriched product is desired, the sorbent is typically regenerated following $CHF_2CHF_2$ removal by desorption of sorbent materials. Desorption of components held by the sorbent may be effected with the sorbent left in place, or the sorbent may be removed and the desorption effected remotely from where the sorption step occurred. These desorbed components may exit the sorbent section in a direction either co-current (in the same direction as the original $C_2H_2F_4$ mixture feed was fed) or countercurrent (in the opposite direction of the original stream requiring separation). Desorption may be effected with or without the use of a supplemental purge liquid or gas flow. Where supplemental purge material is used, it may be a component of the feed, or some appropriate alternative material, such as nitrogen. Such supplemental purge materials may be fed either co-currently or countercurrently.

In general, desorption can be effected by changing any thermodynamic variable which is effective in removing the sorbed components from the sorbent. For example, sorption and desorption may be effected using a thermal swing cycle, (e.g., where after a period of sorption, the sorbent is heated externally through the wall of the vessel containing it, and/or by the feeding of a hot liquid or gas into the sorbent, the hot gas being either one of the component materials or alternative materials). Alternatively, sorbed components can be removed by using a pressure swing cycle or vacuum swing cycle (e.g., where after a period of sorption the pressure is sufficiently reduced, in some embodiments to a vacuum, such that sorbed components are desorbed). Alternatively, the sorbed components can be removed by use of some type of stripping gas or liquid, fed co-currently or countercurrently to the original process feed material. The stripping material may be one of the process feed materials or another material such as nitrogen.

One or several beds of sorbent may be used. Where several beds are used, they may be combined in series or in parallel. Also, where several beds are used, the separation efficiency may be increased by use of cycling zone sorption, where the pressure and or the temperatures of the beds are alternately raised and lowered as the process stream is passed through.

Practice of the invention will be further apparent from the following non-limiting Examples.

EXAMPLE 1

Metal tubing (0.18 inch I.D.×12 inch, 0.46 cm I.D.×30.5 cm) was packed with a carbon sorbent and installed in a gas chromatograph with a flame ionization detector. Helium was fed as a carrier gas at 33 sccm ($5.5 \times 10^{-7}$ m$^3$/s). Samples of the various compounds were then injected into the carrier stream at 200° C. The results of these experiments using Barneby & Sutcliffe Type PE (3.75 g) carbon (Carbon A), Westvaco Microporous Wood-Based Granular Carbon (Carbon B), Barneby & Sutcliffe Type UU (3.85 g) carbon (Carbon C) and Calgon BPL (2.59g) carbon (Carbon D) are shown in Table 1. These data show that in each case the isomers had different retention times, and thus may be separated using the carbons of this Example.

TABLE 1

| Carbon | Sample mL[a] | Retention Time (min.) | | Separation Factor[d] | Na[e] | K[f] |
| --- | --- | --- | --- | --- | --- | --- |
| | | 134[b] | 134a[c] | | | |
| A | 5 | 6.6 | 4.0 | 1.65 | 0.13% | 1.09% |
| | 200 | 4.36 | 3.16 | 1.36 | 0.13% | 1.09% |
| B | 5 | 4.22 | 2.61 | 1.62 | 0.58% | 75 ppm |
| | 200 | 3.32 | 2.27 | 1.46 | 0.58% | 75 ppm |
| C | 200 | 4.79 | 3.38 | 1.42 | 940 ppm | 0.93% |
| D | 5 | 2.32 | 1.75 | 1.32 | 660 ppm | 650 ppm |
| | 200 | 2.01 | 1.59 | 1.26 | 660 ppm | 650 ppm |

[a]Volume of gas sample injected (microliters)
[b]134 = $CHF_2CHF_2$
[c]134a = $CF_3CH_2F$
[d]Separation Factor = 134 retention time/134a retention time
[e]sodium content of carbon in weight percent or parts per million as indicated
[f]potassium content of carbon in weight percent or parts per million as indicated It is evident from Table 1 that the relative sorption efficiency for HFC-134 is higher in the presence of the alkali metals Na and K.

EXAMPLE 2

Metal tubing (0.18 inch I.D.×12 inch, 0.46 cm I.D.×30.5 cm was packed with a carbon sorbent and installed in a gas chromatograph with a flame ionization detector. The experiment was repeated using the same carbon, but washing it with hydrochloric acid before using it for separations. The sodium content of Westvaco Microporous Wood-Based Granular Carbon (Not Acid-Washed, NAW) was 1.29%. After washing with hydrochloric acid the sodium content was 9 ppm. This carbon was designated Acid-Washed (AW). Helium was fed as a carrier gas at 33 sccm ($5.5 \times 10^{-7}$ m$^3$/s). Samples of 134 and 134a were then injected into the carrier stream at 200° C. The results of these experiments are shown in Table 2. These data show that a more efficient separation was obtained with the carbon containing alkali metal; in this case sodium.

TABLE 2

| Carbon | Na Content | Retention Time (min.) 134 | Retention Time (min.) 134a | Separation Factor[a] |
|---|---|---|---|---|
| NAW | 1.29% | 10.67 | 6.63 | 1.61 |
| AW | 9 ppm | 6.2 | 4.3 | 1.44 |

[a]Separation Factor = 134 retention time/134a retention time

EXAMPLE 3

A packed tube (26 cm×2.12 cm I.D) containing Calgon BPL carbon (46.1 g, 4.8×0.59 mm (12×30 mesh)) was purged with nitrogen continuously for 24 hours at 250° C. and at 1 atmosphere pressure. While still being purged with nitrogen, the bed was cooled and was maintained at 25° C. HFC-134a containing 1 wt % HFC-134 was then fed to the bed at 16.7 grams per hour. The results are shown in Table 3.

TABLE 3

| Time (min) | 134a in[a] | 134a out[b] | 134 out[c] |
|---|---|---|---|
| 0 | 0 | 0 | 0 |
| 61 | 0.164 | 0 | 0 |
| 65 | 0.175 | 0.011 | 0 |
| 77 | 0.207 | 0.043 | 0 |
| 89 | 0.239 | 0.075 | 0.61 |
| 100 | 0.269 | 0.105 | 0.88 |
| 112 | 0.301 | 0.137 | 0.96 |
| 124 | 0.334 | 0.170 | 1.00 |

[a]134a in represents the total running sum of the moles of CF$_3$CH$_2$F fed to the column.
[b]134a out represents the total running sum of the moles of CF$_3$CH$_2$F exiting the column.
[c]134 out represents the instantaneous concentration of CHF$_2$CHF$_2$ in the CF$_3$CH$_2$F exiting the column, expressed as a multiple of the 1 wt. % feed (i.e., 0.5 would equal a 0.5 wt. % HFC-134 concentration in the HFC-134a effluent). A zero is less than the detection limit of about 10 ppm.

This example shows that carbon will selectively hold back HFC-134 allowing HFC-134a free of HFC-134 followed by HFC-134a containing reduced HFC-134 concentrations to be obtained.

EXAMPLE 4

A packed tube (26 cm×2.12 cm I.D) containing Barneby & Sutcliffe Type PE carbon (50.3 g) was purged with nitrogen continuously for 12 hours at 250° C. and at atmosphere pressure. While still being purged with nitrogen, the bed was cooled and was maintained at 25° C. HFC-134a containing 1 wt % HFC-134 was then fed to the bed at 16.7 grams per hour. The results are shown in Table 4.

TABLE 4

| Time (min) | 134a in[a] | 134a out[b] | 134 out[c] |
|---|---|---|---|
| 0 | 0 | 0 | 0 |
| 69 | 0.186 | 0 | 0 |
| 73 | 0.196 | 0.010 | 0 |
| 85 | 0.229 | 0.043 | 0 |
| 96 | 0.258 | 0.072 | 0 |
| 108 | 0.291 | 0.105 | 0 |
| 120 | 0.323 | 0.137 | 0.76 |
| 132 | 0.355 | 0.169 | 0.94 |
| 144 | 0.387 | 0.201 | 1.00 |

[a]134a in represents the total running sum of the moles of CF$_3$CH$_2$F fed to the column.
[b]134a out represents the total running sum of the moles of CF$_3$CH$_2$F exiting the column.
[c]134 out represents the instantaneous concentration of CHF$_2$CHF$_2$ in the CF$_3$CH$_2$F exiting the column, expressed as a multiple of the 1 wt. % feed (i.e., 0.5 would equal a 0.5 wt. % HFC-134 concentration in the HFC-134a effluent). A zero is less than the detection limit of about 10 ppm.

EXAMPLE 5

A packed tube (26 cm×2.12 cm I.D) containing Westvaco Microporous Wood-Based Granular Carbon (46 g) was purged with nitrogen continuously for 12 hours at 250° C. and at 1 atmosphere pressure. While still being purged with nitrogen, the bed was cooled and was maintained at 25° C. HFC-134a containing 1 wt % HFC-134 was then fed to the bed at 16.6 grams per hour. The results are shown in Table 5.

TABLE 5

| Time (min) | 134a in[a] | 134a out[b] | 134 out[c] |
|---|---|---|---|
| 0 | 0 | 0 | 0 |
| 74 | 0.199 | 0.003 | 0 |
| 82 | 0.221 | 0.025 | 0 |
| 94 | 0.253 | 0.057 | 0 |
| 106 | 0.285 | 0.089 | 0 |
| 118 | 0.317 | 0.121 | 0.16 |
| 130 | 0.350 | 0.154 | 0.65 |
| 142 | 0.382 | 0.186 | 0.97 |
| 155 | 0.417 | 0.221 | 1.00 |

[a]134a in represents the total running sum of the moles of CF$_3$CH$_2$F fed to the column.
[b]134a out represents the total running sum of the moles of CF$_3$CH$_2$F exiting the column.
[c]134 out represents the instantaneous concentration of CHF$_2$CHF$_2$ in the CF$_3$CH$_2$F exiting the column, expressed as a multiple of the 1 wt. % feed (i.e., 0.5 would equal a 0.5 wt. % HFC-134 concentration in the HFC-134a effluent). A zero is less than the detection limit of about 10 ppm.

EXAMPLE 6

A packed tube (26 cm×2.12 cm I.D) containing Westvaco Microporous Wood-Based Granular Carbon (46 g) was purged with nitrogen continuously for 12 hours at 250° C. and at 1 atmosphere pressure. While still being purged with nitrogen, the bed was cooled and was maintained at 25° C. HFC-134a containing 1 wt % HFC-134 was then fed to the bed at 16.6 grams per hour and at 4.7 atm. (476 kPa). The results are shown in Table 6.

TABLE 6

| Time (min) | 134a in[a] | 134a out[b] | 134 out[c] |
|---|---|---|---|
| 0 | 0 | 0 | 0 |
| 54 | 0.261 | 0.013 | 0 |
| 65 | 0.3125 | 0.067 | 0 |
| 77 | 0.373 | 0.125 | 0 |
| 89 | 0.431 | 0.183 | 0 |
| 101 | 0.489 | 0.241 | 0.33 |
| 113 | 0.547 | 0.299 | 0.47 |
| 125 | 0.605 | 0.357 | 0.55 |
| 137 | 0.663 | 0.415 | 0.82 |

[a]134a in represents the total running sum of the moles of $CF_3CH_2F$ fed to the column.
[b]134a out represents the total running sum of the moles of $CF_3CH_2F$ exiting the column.
[c]134 out represents the instantaneous concentration of $CHF_2CHF_2$ in the $CF_3CH_2F$ exiting the column, expressed as a multiple of the 1 wt. % feed (i.e., 0.5 would equal a 0.5 wt. % HFC-134 concentration in the HFC-134a effluent). A zero is less than the detection limit of about 10 ppm.

Examples 3 through 6 show that these carbon based sorbents will selectively sorb HFC-134 allowing HFC-134a free of HFC-134, followed by HFC-134a containing reduced HFC-134 concentration to be obtained. Examples 3 through 6 show that process material other than the components to be separated can be used to strip HFC-134 (i.e., in this case, nitrogen rather than HFC-134a is used to clear the bed of HFC-134). Also, examples 5 and 6 show that the capacity or 134 increases with pressure, and illustrates the presence of pressure swing adsorption.

EXAMPLE 7

This is an example of a thermal swing cycle alternating a sorption step with a desorption step. The column and carbon packing are the same as that used in Example 4 above. During the sorption step, HFC-134a containing 1 wt % 134 was fed to the packed column at 26° C. and at a feed rate of 16.6 g/hr with a back-pressure setting of 1 atmosphere (101 kPa) in the column. When HFC-134 began to break through at the other end of the column, the flow of feed was stopped, and the ends of the column were sealed. The column was then heated to 150° C., and gas was vented from the column in the direction countercurrent to the original direction of feed, to keep the pressure at 1 atmosphere (101 kPa). When the temperature reached 150° C., HFC-134a containing less than 1 ppm of HFC-134 was fed in the direction countercurrent to the original feed to purge the bed, at 16.5 g/hr and with a back pressure setting of 1 atmosphere (101 kPa). The column valves were then closed at both ends, and the column cooled to 26° C. The cooling of the bed caused a partial vacuum. The pressure was then brought back to 1 atmosphere (101 kPa) using the high HFC-134 content HFC-134a and the cycle was started again. The sorption and desorption steps were then repeated. The results of the second sorption step are shown in Table 7A.

TABLE 7A

| Time (Min) | Temp °C. | HFC-134a in[a] | HFC-134a out[b] | HFC-134 out[c] |
|---|---|---|---|---|
| 0 | 26 | 0 | 0 | 0 |
| 93 | 26 | 0.250 | 0.124 | 0 |
| 117 | 26 | 0.315 | 0.189 | 0.77 |
| 129 | 26 | 0.347 | 0.221 | 0.87 |
| 140 | 26 | 0.377 | 0.251 | 0.96 |

[a]HFC-134a in represents the total running sum of the moles of HFC-134a fed to the column.
[b]HFC-134a out represents the total running sum of the moles of HFC-134a exiting the column.
[c]HFC-134 out represents the instantaneous concentration of the HFC-134 in the HFC-134a exiting the column, expressed as a multiple of the 1% feed. A zero is less than the detection limit of about 10 ppm.

The results of the desorption step which followed are shown in Table 7B.

TABLE 7B

| Time (min) | Temp °C. | HFC-134a in[a] | HFC-134a out[b] | HFC-134 out[c] |
|---|---|---|---|---|
| 0 | 25 | 0 | 0 | 0 |
| 7 | 35 | 0 | 0.049 | 1.16 |
| 12 | 98 | 0 | 0.107 | 1.51 |
| 24 | 150 | 0 | 0.133 | 1.63 |
| 36 | 150 | 0.032 | 0.165 | 1.67 |
| 47 | 150 | 0.062 | 0.195 | 1.63 |
| 71 | 150 | 0.126 | 0.259 | 0 |

[a]HFC-134a in represents the total running sum of the moles of HFC-134a fed to the column.
[b]HFC-134a out represents the total running sum of the moles of HFC-134a exiting the column.
[c]HFC-134 out represents the instantaneous concentration of the HFC-134 in the HFC-134a exiting the column, expressed as a multiple of the 1% feed. A zero is less than the detection limit of about 10 ppm.

Initially, no HFC-134a was fed, but HFC-134a and HFC-134 exited the column due to the let down of the pressure as the temperature was raised from 26° C. to 150° C. Beginning at 24 minutes, when the temperature reached 150° C., HFC-134a containing less than 1 ppm 134 was fed at 16.5 g/hr. At 71 minutes, the HFC-134a flow was stopped.

This example shows the use of a temperature swing cycle as a process concept to produce both HFC-134-free and HFC-134-reduced HFC-134a.

EXAMPLE 8

This is an example of a thermal swing cycle alternating a sorption step with a desorption step. The column and carbon packing were the same as that used in Examples 5 and 6 above. During the sorption step, HFC-134a containing 1 wt % 134 was fed to the packed column at 25° C. and a 134a feed rate of 16.6 g/hr with a back-pressure setting of 1 atmosphere (101 kPa) in the column. When the outlet HFC-134 concentration matched the inlet concentration, the flow of feed was stopped, and the ends of the column were sealed. The column was then heated to 150° C., and gas was vented from the column in the direction countercurrent to the original direction of feed, to keep the pressure at 1 atmosphere (101 kPa). When the temperature reached 150° C., HFC-134a containing less than 1 ppm of HFC-134 was fed in the direction countercurrent to the original feed to purge the bed, at 16.5 g/hr and with a back pressure setting of 1 atmosphere (101 kPa). The column valves were then closed at both ends, and cooled to 25° C. The cooling of the bed caused a partial vacuum. The pressure was then brought back to 1 atmosphere (101 kPa) using the high HFC-134 content HFC-134a and the cycle was started again. The sorption and desorption steps were then repeated.

The results of the second sorption step are shown in Table 8A.

TABLE 8A

| Time (min) | Temp °C. | HFC-134a in[a] | HFC-134a out[b] | HFC-134 out[c] |
|---|---|---|---|---|
| 0 | 25 | 0 | 0 | 0 |
| 29 | 25 | 0.140 | 0 | 0 |
| 73 | 25 | 0.353 | 0.213 | 0 |
| 85 | 25 | 0.411 | 0.271 | 0.25 |
| 97 | 25 | 0.469 | 0.329 | 0.80 |
| 100 | 25 | 0.532 | 0.392 | 1.00 |

[a]HFC-134a in represents the total running sum of the moles of HFC-134a fed to the column.
[b]HFC-134a out represents the total running sum of the moles of HFC-134a exiting the column
[c]HFC-134 out represents the instantaneous concentration of HFC-134 in the HFC-134a exiting the column, expressed as a multiple of the 1% feed. A zero is less than the detection limit of about 10 ppm.

The results of the desorption step which followed are shown in Table 8B.

TABLE 8B

| Time (min) | Temp °C. | HFC-134a in[a] | HFC-134a out[b] | HFC-134 out[c] |
|---|---|---|---|---|
| 0 | 25 | 0 | 0 | 0 |
| 10 | 36 | 0 | 0.049 | 1.09 |
| 22 | 78 | 0 | 0.105 | 1.31 |
| 34 | 130 | 0 | 0.150 | 1.54 |
| 46 | 150 | 0.015 | 0.170 | 1.65 |
| 58 | 150 | 0.073 | 0.228 | 1.59 |
| 71 | 150 | 0.136 | 0.291 | 1.56 |
| 83 | 150 | 0.194 | 0.349 | 0.02 |
| 95 | 150 | 0.252 | 0.407 | 0 |

[a]HFC-134a in represents the total running sum of the moles of HFC-134a fed to the column.
[b]HFC-134a out represents the total running sum of the moles of HFC-134a exiting the column.
[c]HFC-134 out represents the instantaneous concentration of the HFC-134 in the HFC-134a exiting the column, expressed as a multiple of the 1% feed. A zero is less than the detection limit of about 10 ppm.

Initially, no HFC-134a was fed, but HFC-134a and HFC-134 exited the column due to the let down of the pressure as the temperature was raised from 25° C. to 150° C. Beginning at 34 minutes, when the temperature reached 150° C., HFC-134a containing less than 1 ppm 134 was fed at 16.5 g/hr. At 95 minutes, the HFC-134a flow was stopped.

This example shows the use of a temperature swing cycle as a process concept to produce both HFC-134-free and HFC-134-reduced HFC-134a.

EXAMPLE 9

Metal tubing 0.18" (4.6 mm) I.D.×2 ft. (0.51 m) was packed with zeolite sorbents as indicated in Table 9, and installed in a gas chromatograph with a flame ionization detector. The columns were heated at 200° C. in flowing helium for a minimum of 12 hours. Helium was fed as a carrier gas at 20 sccm ($3.3 \times 10^{-7}$ m$^3$/s). Samples (25 µL) of HFC-134 and HFC-134a were then injected into the carrier stream at different temperatures. The results of these experiments are shown in Table 9. Comparison of the 134/134a data for Na-Y and H-Y show a much enhanced separation on the more basic zeolite.

TABLE 9

| Zeolite | Temperature (°C.) | Retention Times (min) 134/134a | Separation Factor |
|---|---|---|---|
| Na—Y | 200 | 408/71.4 | 5.7 |
| H—Y | 100 | 68.1/46.1 | 1.5 |
| H-ZSM-5[a] | 200 | 470/308 | 1.5 |
| 5A | 200 | 291/about 150 | 1.9 |

[a]The flow rate for the H-ZSM-5 run was 35 sccm ($5.8 \times 10^{-7}$ m$^3$/s)

EXAMPLE 10

Metal tubing 0.18" (4.6 mm) I.D.×2 ft. (0.51 m) was packed with zeolite sorbents as indicated in Table 10, and installed in a gas chromatograph with a flame ionization detector. The columns were heated at 200° C. in flowing helium for a minimum of 12 hours. Helium was fed as a carrier gas at 30 sccm ($5.0 \times 10^{-7}$ m$^3$/s). Samples (25 to 500 µL) of HFC-134 and HFC-134a were then injected into the carrier stream at different temperatures. Each test was run in duplicate. Methane (1% in nitrogen) was run as a standard at each temperature. The results of these experiments are shown in Table 10.

TABLE 10

| Zeolite | Temperature (°C.) | Retention Times (min) 134/134a | Separation Factor |
|---|---|---|---|
| Na—Y | 230 | 160/53.2 | 3.0 |
|  | 240 | 128/45.1 | 2.8 |
|  | 250 | 98.3/36.8 | 2.7 |
| H—Y | 210 | 2.07/1.19 | 1.7 |
|  | 220 | 1.78/1.06 | 1.7 |
|  | 230 | 1.01/0.89 | 1.1 |
| H-ZSM-8 | 210 | 110/70.2 | 1.6 |
|  | 220 | 79.7/51.1 | 1.6 |
|  | 230 | 56.7/37.5 | 1.5 |
| 5A | 230 | 74.7/29.4 | 2.5 |
|  | 240 | 64.1/24.9 | 2.6 |
|  | 250 | 49.2/18.5 | 2.7 |

EXAMPLE 11

This is an example of a thermal swing cycle with countercurrent purge during desorption. A 1 inch (2.54 cm) diameter tube was packed with 63 grams of the zeolite H-ZSM-5, and purged with nitrogen at 50 psig (450 kPa). The nitrogen was then turned off, and the column fed with HFC-134a containing 1.2 mole % HFC-134 at 60 sccm ($1.0 \times 10^{-7}$ m$^3$/s) and 50 psig (450 kPa). The results of this test are shown in Table 11A.

TABLE 11A

| Time (min) | Temp °C. | HFC-134 out[a] |
|---|---|---|
| 0 | 29 | — |
| 10 | 29 | — |
| 20 | 29 | 0* |
| 30 | 29 | 0 |
| 40 | 29 | 0 |
| 50 | 29 | 0 |
| 60 | 29 | 0 |
| 70 | 29 | 0 |
| 80 | 29 | 0 |

TABLE 11A-continued

| Time (min) | Temp °C. | HFC-134 out[a] |
|---|---|---|
| 90 | 29 | 0.18 |
| 100 | 29 | 0.34 |
| 110 | 29 | 0.51 |
| 120 | 29 | 0.69 |

*Breakthrough of HFC-134a occurs.
[a]HFC-134 out represents the instantaneous concentration of HFC-134 in the HFC-134a exiting the column, expressed as a multiple of the original 1% feed. A zero is less than the detection limit of about 10 ppm.

When the outlet concentration of the 134 matched the inlet concentration, the high 134 concentration 134a flow was stopped and the ends of the column were sealed. The column was then heated to 150° C., and gas was vented from the column in the direction countercurrent to the original direction of feed, to keep the pressure at 1 atmosphere (100 kPa). When the temperature reached 150° C., HFC-134a containing less than 1 ppm 134 was fed in the direction countercurrent to the original feed at psig (450 kPa). The results are summarized in Table 11B.

TABLE 11B

| Time (min) | Temp °C. | HFC-134 out[a] |
|---|---|---|
| 0 | 31 | 1.06 |
| 10 | 86 | 1.19 |
| 20 | 114 | 1.37 |
| 30 | 126 | 1.56 |
| 40 | 133 | 1.63 |
| 50 | 133 | 1.67 |
| 60 | 133 | 1.75 |
| 70 | 134 | 1.61 |
| 80 | 134 | 1.25 |
| 90 | 134 | 0.78 |
| 100 | 134 | 0.41 |
| 110 | 134 | 0.18 |
| 120 | 134 | 0 |

[a]HFC-134 out represents the instantaneous concentration of the HFC-134 in the HFC-134a exiting the column, expressed as a multiple of the original 1% feed. A zero is less than the detection limit of about 10 ppm.

EXAMPLE 12

This is an example of a thermal swing cycle with countercurrent purge during desorption. A 0.93 inch (2.36 cm) diameter by 12 inch (30.48) long tube was packed with 80 grams of LZ-Y52 zeolite (a Na-Y zeolite), and purged with nitrogen at 50 psig (450 kPa). The nitrogen was then turned off, and the column fed with HFC-134a containing 1.5 mole % HFC-134 at 50 psig (450 kPa) and 30° C. The results of this test are shown in Table 12A.

TABLE 12A

| HFC-134a in[a] | HFC-134a out[b] | HFC-134 out[c] |
|---|---|---|
| 0 | 0 | 0 |
| 0.235 | 0.004 | 0 |
| 0.958 | 0.717 | 0 |
| 0.965 | 0.736 | 0.108 |
| 0.987 | 0.758 | 0.221 |
| 1.009 | 0.781 | 0.304 |
| 1.032 | 0.803 | 0.379 |

TABLE 12A-continued

| HFC-134a in[a] | HFC-134a out[b] | HFC-134 out[c] |
|---|---|---|
| 1.053 | 0.825 | 0.447 |
| 1.071 | 0.843 | 0.460 |

[a]HFC-134a in represents the total running sum of the moles of HFC-134a fed to the column.
[b]HFC-134a out represents the total running sum of the moles of HFC-134a exiting the column.
[c]HFC-134 represents the instantaneous concentration of HFC-134 in the HFC-134a exiting the column, expressed as a multiple of the 1.5% feed.

When the outlet concentration of the 134 reached of the feed concentration, the high 134 concentration 134a flow was stopped and the column heated to 150° C. The pressure generated from the heating was vented from the column in the direction countercurrent to the original direction of feed. During the temperature ramp, approximately 0.0514 moles of 134a and 0.0002 moles of 134 were vented. When the temperature reached 150° C., HFC-134 free HFC-134a was fed in the direction countercurrent to the original feed at psig (450 kPa) and 150° C. The results are summarized in Table 12B.

TABLE 12B

| HFC-134a in[a] | HFC-134a out[b] | HFC-134 out[c] |
|---|---|---|
| 0 | 0 | 0 |
| 0.0336 | 0.0321 | 3.26 |
| 0.0673 | 0.0639 | 3.45 |
| 0.1010 | 0.0958 | 3.48 |
| 0.1347 | 0.1277 | 3.48 |
| 0.1795 | 0.1702 | 3.26 |
| 0.2118 | 0.2009 | 3.05 |
| 0.2513 | 0.2380 | 2.48 |
| 0.3545 | 0.3396 | 0.58 |

[a]HFC-134a in represents the total running sum of the moles of HFC-134a fed to the column.
[b]HFC-134a out represents the total running sum of the moles of HFC-134a exiting the column.
[c]HFC-134 represents the instantaneous concentration of HFC-134 in the HFC-134a exiting the column, expressed as a multiple of the 1.5% feed.

EXAMPLE 13

Metal tubing 0.18" (4.6 mm) I.D.×2 ft. (0.51 m) was packed with zeolite sorbents as indicated in Table 13 and installed in a gas chromatograph with a flame ionization detector. The columns were heated at 200° C. in flowing helium for a minimum of 12 hours. Helium was fed as a carrier gas at 30 sccm ($5.0 \times 10^{-7}$ m$^3$/s). Samples (5 to 25 μL) of HFC-134 and HFC-134a were then injected into the carrier stream at different temperatures. Each test was run in duplicate. Methane (1% in nitrogen) was run as a standard at each temperature. The results of these experiments are shown in Table 13.

TABLE 13

| Zeolite | Temperature (°C.) | Retention Times (min) 134/134a | Separation Factor |
|---|---|---|---|
| ETS-10[a] | 200 | 262.5/90.3 | 2.9 |
| Na-A | 200 | 1.6/0.6 | 2.7 |
| Clinoptilolite | 200 | 1.0/0.8 | 1.3 |
| Ferrierite | 200 | 0.9/0.5 | 1.8 |

[a]Sodium Potassium Titanosilicate

EXAMPLE 14

Metal tubing 0.18" (4.6 mm) I.D.×4.5 in (11.4 cm) was packed with Zeolite Na-X as indicated in Table 14, and installed in a gas chromatograph with a flame ionization detector. The columns were heated at 200° C. in flowing helium for a minimum of 12 hours. Helium was fed as a carrier gas at 30 sccm ($5.0 \times 10^{-7}$ m$^3$/s). Samples (25 µL) of HFC-134 and HFC-134a were then injected into the carrier stream at different temperatures. Each test was run in duplicate. Methane (1% in nitrogen) was run as a standard at each temperature. The results of these experiments are shown in Table 14. The peaks were very broad and therefore the retention times were difficult to measure. However, it was clear that the relative retention times of the 134/134a isomers were reversed when compared to the previous examples.

TABLE 14

| Zeolite | Temperature (°C.) | Retention Times (min) 134/134a | Separation Factor |
|---|---|---|---|
| Na-X | 200 | 13.2/180.7 | 0.073 |
| Na-X | 210 | 60.0/115.0 | 0.52 |

The examples serve to illustrate particular embodiments of the invention. The invention is not confined thereto, but embraces embodiments which come within the scope of the claims.

What is claimed is:

1. A process for separating a mixture of $CHF_2CHF_2$ and $CF_3CH_2F$ to provide a product wherein the mole ratio of $CF_3CH_2F$ relative to $CHF_2CHF_2$ is increased, comprising the step of: contacting said mixture with a sorbent for $CHF_2CHF_2$ selected from the group consisting of (i) inorganic molecular sieves having intermediate electronegativities greater than the intermediate electronegativity of Zeolite Na-X and (ii) activated carbons, at a temperature within the range of –20° C. to 300° C. and a pressure within the range of 10 kPa to 3000 kPa and for a period of time sufficient to remove a substantial amount of the $CHF_2CHF_2$ and increase the mole ratio of $CF_3CH_2F$ to $CHF_2CHF_2$ by at least about 25% relative to the mole ratio thereof in the initial mixture.

2. The process of claim 1 wherein the mixture separated has a mole ratio of $CF_3CH_2F$ to $CHF_2CHF_2$ of at least about 9:1 and at least about 50 mole percent of the $CHF_2CHF_2$ is removed.

3. The process of claim 2 where sufficient contact with said sorbent is provided to produce $CF_3CH_2F$ of at least about 99.99 mole percent purity.

4. A process for separating a mixture of $CHF_2CHF_2$ and $CF_3CH_2F$ to provide a product wherein the mole ratio of $CHF_2CHF_2$ relative to $CF_3CH_2F$ is increased comprising the step of: contacting said mixture with a sorbent for $CHF_2CHF_2$ selected from the group consisting of (i) inorganic molecular sieves having intermediate electronegativities greater than the intermediate electronegativity of Zeolite Na-X and (ii) activated carbons, at a temperature within the range of –20° C. to 300° C. and a pressure within the range of 10 kPa to 3000 kPa and for a period of time sufficient to remove a substantial amount of the $CHF_2CHF_2$; and desorbing sorbed $CHF_2CHF_2$ to provide a product which is enriched therewith.

5. The process of claim 1, claim 2, claim 3, or claim 4 wherein the sorbent is a zeolite having an average pore size of from 0.3 to 1.5 nanometers.

6. The process of claim 1, claim 2, claim 3, or claim 4 wherein the sorbent is a Zeolite Y, a Zeolite A, a Zeolite ZSM-5, or a Zeolite ZSM-8.

7. The process of claim 1, claim 2, claim 3, or claim 4 wherein the sorbent is an activated carbon.

8. The process of claim 7 wherein the carbon contains from about 0.5 to 3 weight percent inherent metal selected from the group consisting of lithium, sodium, potassium, rubidium, cesium, magnesium, calcium, strontium, barium, and combinations thereof.

9. The process of claim 7 wherein the carbon contains from about 0.5 to 3 weight percent of inherent metals selected from the group consisting of sodium, potassium, and combinations thereof.

10. A process for producing $C_2H_2F_4$ by hydrogenolysis of $C_2Cl_2F_4$ characterized by the step of: contacting a mixture of $CHF_2CHF_2$ and $CF_3CH_2F$ produced by said hydrogenolysis with a sorbent for $CHF_2CHF_2$ selected from the group consisting of (i) inorganic molecular sieves having intermediate electronegativities greater than the intermediate electronegativity of Zeolite Na-X and (ii) activated carbons, at a temperature within the range of –20° C. to 300° C. and a pressure within the range of 10 kPa to 3000 kPa and for a period of time sufficient to remove a substantial amount of the $CHF_2CHF_2$; and either (i) recovering a product wherein the mole ratio of $CF_3CH_2F$ relative to $CHF_2CHF_2$ is increased, (ii) desorbing sorbed $CHF_2CHF_2$ to provide a product wherein the mole ratio to $CHF_2CHF_2$ relative to $CF_3CH_2F$ is increased, or both.

* * * * *